United States Patent [19]

Oplinger et al.

[11] Patent Number: 6,090,846
[45] Date of Patent: *Jul. 18, 2000

[54] SUBSTITUTED UREA AND ISOTHIOUREA DERIVATIVES AS NO SYNTHASE INHIBITORS

[75] Inventors: Jeffrey Alan Oplinger; Barry George Shearer, both of Cary; Eric Steven Furfine, Durham; Edward Patrick Garvey, Chapel Hill, all of N.C.

[73] Assignee: Glaxo Wellcome Inc., Research Triangle Park, N.C.

[*] Notice: This patent issued on a continued prosecution application filed under 37 CFR 1.53(d), and is subject to the twenty year patent term provisions of 35 U.S.C. 154(a)(2).

[21] Appl. No.: 08/615,291

[22] PCT Filed: Oct. 3, 1994

[86] PCT No.: PCT/GB94/02138

§ 371 Date: Mar. 28, 1996

§ 102(e) Date: Mar. 28, 1996

[87] PCT Pub. No.: WO95/09619

PCT Pub. Date: Apr. 13, 1995

[30] Foreign Application Priority Data

Jun. 1, 1994 [EP] European Pat. Off. .............. 94303939

[51] Int. Cl.[7] ....................... A61K 31/215; C07C 335/00
[52] U.S. Cl. .............................................. 514/508; 558/4
[58] Field of Search ........................... 558/5, 8; 562/624; 514/508

[56] References Cited

U.S. PATENT DOCUMENTS

| 2,849,306 | 8/1958 | Searle .......................................... 71/2.6 |
| 3,202,660 | 8/1965 | Zeile et al. ................................ 260/254 |
| 3,935,266 | 1/1976 | Hashimoto et al. .................. 260/561 A |
| 5,364,881 | 11/1994 | Griffith et al. ............................ 514/508 |

FOREIGN PATENT DOCUMENTS

| 0 202 157 | 11/1986 | European Pat. Off. . |
| 0 392 802 | 10/1990 | European Pat. Off. . |
| 0 411 615 | 2/1991 | European Pat. Off. . |
| 0411615 | 2/1991 | European Pat. Off. . |
| 0 446 699 | 9/1991 | European Pat. Off. . |
| 0446699 | 9/1991 | European Pat. Off. . |
| 1 532 212 | 7/1968 | France . |
| 1532212 | 7/1968 | France . |
| 7 703 011 | 9/1977 | Netherlands . |
| 1 178 242 | 1/1970 | United Kingdom . |
| 2 240 041 | 7/1991 | United Kingdom . |
| WO 91/04024 | 4/1991 | WIPO . |

OTHER PUBLICATIONS

Joshua et al., J. Indian Chem. Soc., vol. 67(9), pp. 759–763, 1990.
Ziegler et al., Monatsh. Chem., vol. 99(4), pp. 1499–1506, 1968.
Loev et al., "Amidines. 3. Thioureas possessing anithypertensive activity". J. Med. Chem., vol. 15(10), pp. 1024–1027, 1972.
Manley et al., Journal of Medicinal Chemistry, vol. 35, 1992, 2327–2340.
Rasmussen et al., Synthesis, vol. 6, Jun. 1988, 460–466.
Dawson et al., Proceedings National Academy of Sciences USA, vol. 88, Jul. 1991, 6368–6371.
Bredt et al., Proc. Natl. Acad. Sci. USA 87:682 (1990).
Science & Technology Concentrates, C&EN, Apr. 4, 1994, p. 24.
Feldman, Tetra. Lttrs., 32(7):875 (1991).
MacAllister, et al., Endothelium 1(supp):s17 #63 (1993).
Griffith, Endothelium 1(supp):s 17 #64 (1993).
Boucher, et al., Endothelium 1(supp):s17 #65 (1993).
Schmid, et al., Endothelium 1(supp):s17 (1993).
Mayer, et al., Febs Letters 288(1.2):187 (1991).
Mondada, et al., Biochemical Pharmacology 38(11):1709 (1989).
Moncada et al., Pharmacological Reviews 43(2):109 (1991).
Narayanan et al., J. Med. Chem. 37:885 (1994).
Nowicki et al., European J. Pharmacology 204:339 (1991).
Schmidt et al., Proc. Natl. Acad. Sci. USA 88:365 (1991).

Primary Examiner—Jose' G. Dees
Assistant Examiner—Barbara Badio
Attorney, Agent, or Firm—Lorie Ann Morgan

[57] ABSTRACT

The use of an N-substituted urea derivative for the manufacture of a medicament for the treatment of a condition where there is an advantage in inhibiting the NO synthase enzyme, in particular cerebral ischemia, and pharmaceutical formulations therefor are disclosed. Novel N-substituted urea derivatives and processes for the preparation thereof are also described.

3 Claims, No Drawings

SUBSTITUTED UREA AND ISOTHIOUREA DERIVATIVES AS NO SYNTHASE INHIBITORS

This application is a 371 of PCT/GB94/02138 filed Oct. 3, 1994, which claims priority to U.S. application Ser. No. 08/131,794 filed Oct. 4, 1993, now abandoned.

The present invention relates to N-substituted urea derivatives, to methods for their manufacture, to pharmaceutical compositions containing them and to their use in therapy, in particular their use as inhibitors of nitric oxide synthase, and in particular neuronal nitric oxide synthase.

It has been known since the early 1980's that the vascular relaxation brought about by acetylcholine is dependent on the presence of the endothelium and this activity was ascribed to a labile humoral factor termed endothelium-derived relaxing factor (EDRF). The activity of nitric oxide (NO) as a vasodilator has been known for well over 100 years and NO is the active component of amyl nitrite, glyceryltrinitrite and other nitrovasodilators. The recent identification of EDRF as NO has coincided with the discovery of a biochemical pathway by which NO is synthesised from the amino acid L-arginine by the enzyme NO synthase.

NO is the endogenous stimulator of the soluble guanylate cyclase and is involved in a number of biological actions in addition to endothelium-dependent relaxation including cytotoxicity of phagocytic cells and cell-to-cell communication in the central nervous system (see Moncada et al, *Biochemical Pharmacology*, 38, 1709–1715 (1989) and Moncada et al, *Pharmacological reviews*, 43, 109–142 (1991)). It is now thought that excess NO production may be involved in a number of conditions, particularly conditions which involve systemic hypotension such as toxic shock and therapy with certain cytokines.

The synthesis of NO from L-arginine can be inhibited by the L-arginine analogue $N^G$-monomethyl-L-arginine (L-NMMA) and the therapeutic use of L-NMMA for the treatment of toxic shock and other types of systemic hypotension has been proposed (WO 91/04024 and GB-A-2240041). The therapeutic use of certain other NO synthase inhibitors apart from L-NMMA for the same purpose has also been proposed in WO 91/04024 and in EP-A-0446699. Other potent NO synthase inhibitors are described in Narayanan et al., J. Med. Chem. 37, 885–887 (1994).

It has recently become apparent that there are at least three types of NO synthase enzymes as follows:

(i) a constitutive, $Ca^{++}$/calmodulin dependent enzyme, located in the endothelium, that releases NO in response to receptor or physical stimulation.

(ii) a constitutive, $Ca^{++}$/calmodulin dependent enzyme, located in the brain, that releases NO in response to receptor or physical stimulation.

(iii) a $Ca^{++}$ independent enzyme which is induced after activation of vascular smooth muscle, macrophages, endothelial cells, and a number of other cells by endotoxin and cytokines. Once expressed this inducible NO synthase synthesises NO for long periods.

The NO released by the constitutive enzyme acts as a transduction mechanism underlying several physiological responses. The NO produced by the inducible enzyme is as a cytotoxic molecule for tumour cells and invading microorganisms. It also appears that the adverse effects of excess NO production, in particular pathological vasodilation and tissue damage, may result largely from the effects of NO synthesised by the inducible NO synthase.

It is believed that NO synthesis plays an important part in the pathology of a range of diseases of the nervous system, eg. ischemia. However, non-selective inhibitors of NO synthases cause profound changes in blood pressure and blood flow, including cerebral blood flow. Unfortunately, ischemic injury inherently reduces the blood supply to the brain and any further decrease in blood flow caused by a non-selective NO synthase inhibitor would have a deleterious effect, potentially opposing any beneficial effect of decreased NO production within the brain. Nevertheless, studies of middle cerebral artery occlusion in both rats and mice have demonstrated a substantial protection effect of low doses of NO synthase inhibitors (see for example Nowicki et al, Eur. J Pharmacol., 1991, 204, 339–340). At high doses, or in models of global ischemia, these inhibitors fail to provide protection. Thus, there is a need for a potent inhibitor of neuronal NO synthase with preferably little or no activity against the vascular endothelial NO synthase.

The NO synthase inhibitors proposed for therapeutic use so far, such as L-NMMA and L-NAME (L-nitroarginine methyl ester), are non-selective in that they inhibit all NO synthase enzymes identified to date. Use of such a non-selective NO synthase inhibitor would require great care to be taken in order to avoid the potentially serious consequences of over-inhibition of the other enzymes. Thus, whilst non-selective NO synthase inhibitors have therapeutic utility provided that appropriate precautions are taken, NO synthase inhibitors which are selective in the sense that they inhibit one NO synthase enzyme to a considerably greater extent compared to one or more of the other enzymes would be of even greater therapeutic benefit and much easier to use.

Unpublished PCT patent application PCT/GB93/02437 discloses a class of S-substituted isothiourea derivatives which inhibit the NO synthase enzymes, showing a slight selectivity of the inducible enzyme over the constitutive enzymes.

It has been found that a class of N-substituted urea derivatives or salts, esters or amides thereof are NO synthase inhibitors, showing selectivity of the neuronal NO synthase enzyme over the endothelial and inducible NO synthase enzymes. The term "urea derivatives" when used herein means "isothiourea derivatives" and "isourea derivatives".

In one aspect the present invention provides the use of an N-substituted urea derivative or a salt, ester or amide thereof, other than N-(2,6-dimethylphenyl)-5,6-dihydro4H-1,3-thiazin-2-amine, for the manufacture of a medicament for the treatment of a condition where there is an advantage in inhibiting the neuronal NO synthase enzyme with less inhibition of the endothelial or inducible NO synthase enzymes.

In another aspect, the present invention provides a method of treatment of a condition where there is an advantage in inhibiting the neuronal NO synthase enzyme with less inhibition of the endothelial or inducible NO synthase enzyme comprising administering to a mammal in need thereof a therapeutically effective amount of an N-substituted urea derivative or a salt, ester or amide thereof, other than N-(2,6-dimethylphenyl)-5,6-dihydro4H-1,3-thiazin-2-amine.

More specifically, the present invention provides the use of a N-substituted urea derivative or salt, ester or amide thereof other than N-(2,6-dimethylphenyl)-5,6-dihydro-4H-1,3-thiazin-2-amine for the manufacture of a medicament for the treatment of a disease of the nervous system due to over production of the neuronal nitric oxide synthase enzyme. Such diseases include cerebral ischemia, CNS trauma, epilepsy, AIDS dementia, chronic neurodegenerative disease and chronic pain, and conditions in which non-adrenergic non-cholinergic nerve may be implicated such as priapism, obesity and hyperphagia, particularly cerebral ischemia.

In one embodiment of the present invention the N-substituted urea derivative is an N-substituted isothiourea derivative, other than N-(2,6-dimethylphenyl)-5,6-dihydro4H-1,3-thiazin-2-amine, preferably an N,S-disubstituted isothiourea derivative. In a second embodiment of the present invention the N-substituted urea derivative is an N-substituted isourea, preferably an N,O-disubstituted isourea derivative.

Preferred urea derivatives include those of the formula (I)

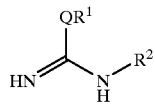

(I)

wherein
Q is oxygen or sulphur
$R^1$ is hydrogen or $C_{1-8}$ hydrocarbyl;
$R^2$ is a mono- or bicyclic heterocyclic ring system, a $C_{1-10}$ hydrocarbyl group which may optionally contain an oxygen atom, a group $S(O)_n$ wherein n is 0, 1 or 2, or a group $NR^3$ wherein $R^3$ is hydrogen or a $C_{1-6}$ aliphatic group, each group $R^2$ optionally being substituted by one to five groups independently selected from
  (i) $C_{1-6}$ alkyl or $C_{3-6}$ cycloalkyl each optionally substituted by one to three halo atoms;
  (ii) a group $OR^4$ wherein $R^4$ is hydrogen, $C_{1-6}$ alkyl, phenyl or benzyl;
  (iii) a halo atom;
  (iv) a group $CO_2R^5$ wherein $R^5$ is hydrogen or $C_{1-4}$ alkyl;
  (v) a group $NR^6R^7$ wherein $R^6$ and $R^7$ are independently selected from hydrogen, $C_{1-4}$ alkyl or a group

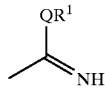

wherein Q and $R^1$ are as hereinbefore defined;
  (vi) nitro; or
  (vii) cyano;
or $R^1$ may be linked to the imino nitrogen to form a monocyclic heterocyclic ring; with the exception of N-(2,6-dimethylphenyl)-5,6-dihydro4H-1,3-thiazin-2-amine.

A preferred group of compounds are those of formula (I) with the proviso that when Q is sulphur and $R^1$ is hydrogen or $C_{1-5}$ alkyl, $R^2$ is not an ornithine or lysine derivative optionally substituted by a $C_{1-6}$ alkyl group on either the α-, β- or γ-carbon atoms, or a tautomer thereof.

One embodiment of the present invention provides compounds of formula (I) as hereinbefore defined with the proviso that $R^1$ is not linked to the imino nitrogen to form a monocyclic heterocyclic ring.

In one preferred embodiment, Q is oxygen.
In a second preferred embodiment, Q is sulphur.
When Q is either oxygen or sulphur:
  suitably $R^1$ is hydrogen, $C_{1-4}$ alkyl, $C_{2-5}$ alkenyl or benzyl; preferably $R^1$ is $C_{1-4}$ alkyl for example ethyl;
  suitably, $R^2$ is a 5- or 6- membered heterocyclic ring or a 9- or 10-membered bicyclic heterocyclic ring, a phenyl ring, or a $C_{2-8}$ alkyl chain which optionally contains a group $S(O)_n$ as hereinbefore defined, or a $C_{2-4}$ alkyl chain which contains a phenylene ring, each group $R^2$ optionally being substituted by one to five groups independently selected from
  (i) a $C_{1-4}$ alkyl group optionally substituted by one to three fluoro atoms:
  (ii) a cyclohexyl ring;
  (iii) a group $OR^{4a}$ wherein $R^{4a}$ is hydrogen, methyl, ethyl, phenyl or benzyl;
  (iv) fluoro, chloro or bromo;
  (v) a group $CO_2R^{5a}$ wherein $R^{5a}$ is hydrogen, methyl or ethyl;
  (vi) a group $NR^{6a}R^{7a}$ wherein $R^{6a}$ and $R^{7a}$ are independently selected from hydrogen, methyl or ethyl or one of $R^{6a}$ and $R^{7a}$ is a group

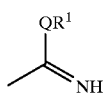

as hereinbefore defined and the other is hydrogen;
  (vii) nitro; or
  (viii) cyano;
or $R^1$ may be linked to the imino nitrogen in the compound of formula (I) to form a thiazole or thiazoline ring.

Formula (I) includes compounds of formulae (IA) to (IF)

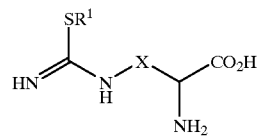

(IA)

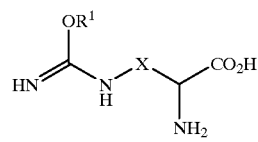

(IB)

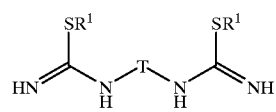

(IC)

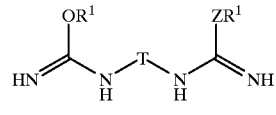

(ID)

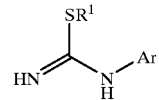

(IE)

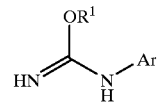

(IF)

wherein Z is oxygen or sulphur; $R^1$ is as hereinbefore defined; X is a $C_{2-9}$ hydrocarbyl group which may optionally contain an oxygen atom, a group $S(O)_n$ as hereinbefore defined, or a group NR$^3$ as hereinbefore defined; T is a C$_{1-8}$ hydrocarbyl group optionally containing a 5- or 6-membered heterocyclic ring, or T is a C$_{2-4}$ hydrocarbyl group containing a phenylene ring; and Ar is a mono- or bicyclic aromatic ring system optionally substituted by one to five groups selected from (i) C$_{1-6}$ alkyl or C$_{3-6}$ cycloalllyl each optionally substituted by one to three halo atoms;

(ii) a group OR$^4$ wherein R$^4$ is hydrogen, C$_{1-6}$ alkyl, phenyl or benzyl;

(iii) a halo atom;

(iv) a group CO$_2$R$^5$ wherein R$^5$ is hydrogen or C$_{1-4}$ alkyl;

(v) a group NR$^6$R$^7$ wherein R$^6$ and R$^7$ are independently selected from hydrogen, C$_{1-4}$ alkyl or a group

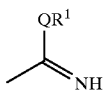

wherein Q and R$^1$ are as hereinbefore defined;

(vi) nitro; or (vii) cyano;

In the formulae (IA) to (IF);

Suitably, R$^1$ is a C$_{1-6}$ hydrocarbyl group, preferably a C$_{1-4}$ alkyl group, e.g. ethyl.

Suitably, X is a C$_{2-6}$ hydrocarbyl group and preferably a C$_{3-5}$ alkylene or alkenylene group.

Suitably, T is C$_{1-8}$ hydrocarbyl containing a 5- or 6-membered heterocyclic ring; or a C$_{2-4}$ hydrocarbyl group containing a phenylene ring.

Suitably Ar is phenyl optionally substituted by one to three substituents which may be the same or different and are selected from C$_{1-4}$ alkyl or C$_{3-6}$ cycloalkyl groups each optionally substituted by one to three halo atoms; C$_{1-4}$ alkoxy groups; hydroxy groups, benzyloxy groups; halo atoms; CO$_2$R$^5$ groups wherein R$^5$ is hydrogen or C$_{1-4}$ alkyl; groups NR$^6$R$^7$ wherein R$^6$ and R$^7$ are independently selected from hydrogen or C$_{1-4}$ alkyl. Most suitably Ar is phenyl substituted by one or two substituents, preferably one substituent.

Preferably Ar is phenyl substituted by C$_{1-3}$ alkoxy, hydroxy, benzyloxy, halo atoms or C$_{1-4}$ alkyl optionally substituted by one to three fluoro atoms, C$_{1-3}$ alkoxy, hydroxy, benzyloxy, or halo atoms.

One preferred embodiment of the present invention includes compounds of formula (IA) wherein X is a C$_{2-9}$ hydrocarbyl group which contains an oxygen atom, a group S(O)$_n$ or NR$^3$ wherein n and R$^3$ are as hereinbefore defined, and compounds of formulae (IB) to (IF) as hereinbefore defined.

Suitable compounds of the formula (I) include:
S-Ethyl-N-(4-phenoxyphenyl)isothiourea
S-ethyl-N-(3-methoxyphenyl)isothiourea
S-ethyl-N-[4-(benzyloxy)phenyl]isothiourea
S-ethyl-N-[4-(ethoxycarbonyl)phenyl]isothiourea
S-ethyl-N-(4-carboxyphenyl)isothiourea
S-ethyl-N-(3-carboxyphenyl)isothiourea
S-ethyl-N-(2-bromophenyl)isothiourea
S-ethyl-N-(4-dimethylaminophenyl)isothiourea
S-ethyl-N-(4-cyclohexylphenyl)isothiourea
S-ethyl-N-(4-hydroxyphenyl)isothiourea
S-ethyl-N-(4-methoxyphenyl)isothiourea
S-ethyl-N-(2-pyridyl)isothiourea
S-Ethyl-N-[4-trifluoromethyl)phenyl]isothiourea
S-Benzyl-N-[4-(trifluoromethyl)phenyl]isothiourea
S-Ethyl-N-(3-chlorophenyl)isothiourea
S-Ethyl-N-(2-isopropylphenyl)isothiourea
S-Ethyl-N-(4-isopropylphenyl)isothiourea
S-Ethyl-N- [3 -(trifluoromethyl)phenyl]isothiourea
S-Ethyl-N-[2-(trifluoromethyl)phenyl]isothiourea
S-Ethyl-N-[2-(chlorophenyl)isothiourea
S-Ethyl-N-(2-methoxyphenyl)isothiourea
S-Ethyl-N-(4-methylphenyl)isothiourea
S-Ethyl-N-(3 -pyridyl)isothiourea
S-Ethyl-N-(4-chloro-3-(trifluoromethyl)phenyl) isothiourea
S-Ethyl-N-(2-chloro-5-(trifluoromethyl)phenyl) isothiourea
S-Ethyl-N-(3-pyridyl)isothiourea
S-Ethyl-N-(4-pyridyl)isothiourea
O-Methyl-N-(4-(trifluoromethyl)phenyl)isourea
O-Ethyl-N-(4-(trifluoromethyl)phenyl)isourea
S-Ethyl-N-[4-(trifluoromethoxy)phenyl]isothiourea
N5-(2-thiazolin-2-yl)-L-ornithine
N6-(2-thiazolin-2-yl)-L-lysine
N,N'-((methylthio)iminomethyl)-m-xylylenediamine
N,N-((methylthio)iminomethyl)-p-xylylenediamine
N5-(imino(methylthio)methyl-L-ornithine
N5-((ethylthio)iminomethyl)-L-ornithine
N6-(imino(methylthio)methyl)-L-lysine
N6-((ethylthio)iminomethyl)-L-lysine
N5-(imino(1 -methylethylthio)methyl)-L-ornithine
N6-(imino( 1-methylethylthio)methyl)-L-lysine
N5-(imino(2-methylpropylthio)methyl)-L-ornithine
N6-(imino(2-methylpropylthio)methyl)-L-lysine
N5-((methylthio)iminomethyl)-D-ornithine
N6-((methylthio)iminomethyl)-D-lysine
N5-((ethylthio)iminomethyl)-D-ornithine
N6-((ethylthio)iminomethyl)-D-lysine
N5-(imino(1-methylethylthio)methyl)-D-ornithine
N6-((1-methylethyl)iminomethyl)-D-lysine
N5-((2-methylpropylthio)iminomethyl)-D-ornithine
N6-((methylpropylthio)iminomethyl)-D-Iysine
N5-(iminomethoxymethyl)-L-ornithine
N5-(ethoxyiminomethyl)-L-ornithine
N5-(iminoisopropoxymethyl)-L-ornithine
N6-iminomethoxymethyl)-L-lysine
N6-(ethoxyiminomethyl)-L-lysine
1-(3-(Aminomethyl)benzyl)-O-ethylisourea
1-(3-(Aminomethyl)benzyl)-S-methylisothiourea
1-(3-(Aminomethyl)benzyl)-S-ethylisothiourea
1-(4-(Aminomethyl)benzyl)-S-methylisothiourea
1-(4-(Aminomethyl)benzyl)-S-ethylisothiourea
S-ethyl-N-(4-diethylamino)phenyl) isothiourea
S-ethyl-N-(5-chloro-2-pyridyl)isothiourea
S-ethyl-N-(4-nitrophenyl) isothiourea
S-ethyl-N-(4-chlorophenyl) isothiourea
S-ethyl-N-(3, 4-dichlorophenyl) isothiourea
S-benzyl-N-phenyl isothiourea
S-ethyl-N-phenyl isothiourea
and salts, esters or amides thereof.

By the term "hydrocarbyl" group is meant a group that contains only carbon and hydrogen atoms and may contain double and/or triple bonds and which may be cyclic or aromatic in nature. An oxygen atom, or a group S(O)$_n$ or NR$^3$ as hereinbefore defined, may optionally intersperse the carbon atoms in the hydrocarbyl chain.

By the term "aliphatic" is meant an alkyl, alkenyl, alkynyl or cycloalkyl group. The terms alkyl, alkenyl and allynyl are intended to include both straight and branched chain variants.

By the term "heterocyclic ring" is meant a cyclic compound containing one to three heteroatoms selected from oxygen, sulphur and nitrogen, and preferably nitrogen and sulphur.

The compounds of formula (I) may include a number of asymmetric centres in the molecule depending on the precise meaning of the various groups and the present invention is intended to include all possible isomers.

When $R^1$ is hydrogen, compounds of formula (I) may exist in tautomeric form and the present invention includes all such forms.

Certain compounds of formula (I) have also been found to have activity against the inducible NO synthase enzyme and may be of use in the treatment of systemic hypotension associated with septic and/or toxic shock induced by a wide variety of agents, therapy with cytokines such as TNF, IL-1 and IL-2 and therapy with cytokine-inducing agents such as 5,6-dimethylxanthenone acetic acid, as an adjuvant to short term immunosuppression in transplant therapy, and in the treatment of autoimmune and/or inflammatory conditions affecting the joints, for example arthritis. Accordingly, the present invention further provides the use of a compound of formula (I) other than 5-methyl-2-(2-thiazolylamino)phenol and S-ethyl-N-phenylisothiourea for the manufacture of a medicament for the treatment of a condition requiring inhibition of the inducible NO synthase enzyme.

In a further aspect the present invention provides a N-substituted urea derivative of formula (I) other than S-ethyl-N-phenylisothiourea, S-ethyl-N-(2-chlorophenyl) isothiourea, S-ethyl-N-(2-trifluoromethylphenyl) isothiourea, 2-propenylthiourea, N-(2,6-dimethylphenyl)-5,6-dihydro4H-1,3-thiazin-2-amine and 5-methyl-2-(2-thiazolyl amino)phenol, or a pharmaceutically acceptable salt, ester or amide thereof for use in medicine.

The present invention also provides a N-substituted urea derivative of formula (I) or a salt, ester or amide thereof, with the proviso that:

(a) when Q is sulphur and
(i) $R^1$ is methyl, $R^2$ is not a phenyl ring substituted by 3-chloro, 2-ethyl, 2-chloro-5-trifluoromethyl, 3-trifluoromethyl, 3-methyl. 3-bromo, 4-nitro, 4-chloro, 3,4-dichloro or $CO_2H$; or $R^2$ is not a group 5-chloro-2-pyridyl;
(ii) $R^1$ is ethyl, $R^2$ is not a phenyl ring or a phenyl ring substituted by 4-methoxy, 2-chloro, 4-hydroxy, 2-methoxy 4-methyl, 2-trifluoromethyl or 3-trifluoromethyl; or (b) the compound of formula (I) is not 2-propenylthiourea N-(2,6-dimethylphenyl)-5,6-dihydro4H- 1,3-thiazin-2-amine 5-methyl-2-(2-thiazolylamino)phenol.

The present invention includes N-substituted urea derivatives in the form of salts, esters or amides, in particular acid addition salts. Suitable salts include those formed with both organic and inorganic acids. Such acid addition salts will normally be pharmaceutically acceptable although salts of non-pharmaceutically acceptable salts may be of utility in the preparation and purification of the compound in question. Thus, preferred salts include those formed from hydrochloric, hydrobromic, sulphuric, citric, tartaric, phosphoric, lactic, pyruvic, acetic, trifluoroacetic, succinic, oxalic, fumaric, maleic, oxaloacetic, methanesulphonic, ethanesulphonic, p-toluenesulphonic, benzenesulphonic and isethionic acids. Salts of N-substituted urea derivatives can be made by reacting the appropriate compound in the form of the free base with the appropriate acid. Esters are pharmaceutically acceptable esters, for example $C_{1-4}$ alkyl esters.

As used herein, reference to "treatment" of a patient is intended to include prophylaxis.

The activity of compounds of formula (a) as inhibitors of isolated NO synthase enzymes has been demonstrated against NO synthase enzymes isolated from the human placenta, the human brain and carcinoma cells.

Whilst it may be possible for the compounds of formula (I) to be administered as the raw chemical, it is preferable to present them as a pharmaceutical formulation. According to a further aspect, the present invention provides a pharmaceutical formulation comprising a compound of formula (I) or a pharmaceutically acceptable salt, ester or amide thereof, other than S-ethyl-N-phenylisothiourea, S-ethyl-N-(2-chlorophenyl)isothiourea, S-ethyl-N-(2-trifluoro methylphenyl)isothiourea, 2-propenyl thiourea, N-(2,6-dimethylphenyl)-5,6-dihydro4H-1,3-thiazin-2-amine and 5-methyl-2-(2-thiazolylamino)phenol, together with one or more pharmaceutically acceptable carriers therefor and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of formula (I) or a pharmaceutically acceptable salt, ester or amide thereof ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example, saline, or water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds of the invention may be administered orally or via injection at a dose of from 0.1 to 500 mg/kg per day. The dose range for adult humans is generally from 5 mg to 35 g/day, preferably 5 mg to 2 g/day and most preferably 10 mg to 1 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

The compounds of formula (I) are preferably administered orally or by injection (intravenous or subcutaneous). The precise amount of compound administered to a patient will be the responsibility of the attendant physician. However the dose employed will depend on a number of factors, including the age and sex of the patient, the precise disorder being treated, and its severity. Also the route of administration may vary depending on the condition and its severity.

The invention further includes a process for the preparation of the novel compounds of formula (I), analogous to those known in the art for preparing N-substituted ureas.

Thus:
(a) Compounds of formula (I) wherein Q is S may be prepared by the reaction of a compound of formula (II)

$$H_2N-R^2 \qquad (II)$$

wherein $R^2$ is as hereinbefore defined, with a compound having a thiocarbonyl group, followed if necessary by hydrolysis to give a compound of formula (I) wherein $R^1$ is hydrogen or a tautomer thereof, and thereafter the optional conversion to a compound of formula (I) wherein $R^1$ is other than hydrogen by allylation of the sulphur atom of the isothiourea The coupling reaction may be carried out between a compound of formula (II) and a compound having a thiocarbonyl group, for example thiophosgene followed by ammonia as described in Tet. Lett. 1991, 32 (7) 875–878 or a compound of formula (II) and an isothiocyanate, such as benzoyl isothiocyanate. Suitably the reaction is carried out in a polar solvent, such as dichloromethane, chloroform, ethanol or acetone at a non-extreme temperature of from −78° C. to 200° C., for example −5° C. to 10° C. and preferably room temperature. The intermediate thiourea, e.g. benzoylthiourea, may be hydrolysed in a polar solvent such as 10% sodium hydroxide solution at a non-extreme temperature of from −20° C. to 200° C., such as the refluxing solvent temperature.

The alkylation is generally carried out using a compound of formula $R^1$-L, wherein $R^1$ is as hereinbefore defined other than hydrogen and L is a suitable leaving group. Suitable leaving groups include a halo atom, for example iodo.

Compounds of formula (II) are commercially available or may be prepared by methods known in the art.

(b) Compounds of formula (I) wherein Q is O may be prepared by the acid catalysed addition of
(i) an alcohol of formula $R^1$-OH to prepare a compound wherein $R^1$ is as hereinbefore defined other than hydrogen; or
(ii) water to prepare a compound wherein $R^1$ is hydrogen
to a compound of formula (III)

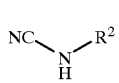

(III)

or a protected derivative thereof, wherein $R^2$ is as hereinbefore defined, followed by deprotection where necessary.

The acid catalysed addition is suitably carried out using the alcohol ($R^1$-OH or water) as the solvent, at a non-extreme temperature of 0° C. to 100° C., and preferably room temperature, in the presence of an acid, e.g. hydrochloric acid, conveniently in solution in ether.

Compounds of formula (III) may be prepared by the reaction of a compound of formula (II) as hereinbefore defined with a compound of formula L'-CN wherein L' is a leaving group, for example a halo atom such as bromo. The reaction may be carried out in ether as a solvent at a non-extreme temperature of from −20° C. to 100° C., suitably 0° C.

The present invention will now be illustrated by way of example only.

Proton ($^1$H) NMR analysis was consistent with the proposed structure in all cases.

EXAMPLE 1

Preparation of S-Ethyl-N-(4-phenoxyphenyl) isothiourea

To a stirred solution of 1-(4-phenoxyphenyl)-2-thiourea (2.00 g, 8.19 mmol) in acetone (20 ml) was added iodoethane (7.61 g, 48.7 mmol). The mixture was heated to reflux for three hours, cooled to room temperature and concentrated at reduced pressure. The resulting viscous oil was crystallized from acetone-pentane to afford S-ethyl-N-(4-phenoxyphenyl)isothiourea hydroiodide as a beige solid. Mp=140–143° C.

The following compounds were made by an analagous method:

| Ex. No. | Compound | MP ° C. |
|---|---|---|
| 1A | S-ethyl-N-(3-methoxyphenyl)isothiourea | 75–77[a] |
| 1B | S-ethyl-N-[4-(benzyloxy)phenyl]isothiourea | 172–174[b] |
| 1C | S-ethyl-N-[4-(ethoxycarbonyl)phenyl]isothiourea | 80–85[a] |
| 1D | S-ethyl-N-(4-carboxyphenyl)isothiourea | 214–215[a] |
| 1E | S-ethyl-N-(3-carboxyphenyl)isothiourea | 149–215[c] |
| 1F | S-ethyl-N-(2-bromophenyl)isothiourea | 89–100[d] |
| 1G | S-ethyl-N-(4-dimethylaminophenyl)isothiourea | 138–141[e] |
| 1H | S-ethyl-N-(4-cyclohexylphenyl)isothiourea | 174–175[a] |
| 1I | S-ethyl-N-(4-hydroxyphenyl)isothiourea | 135[e] |

-continued

| Ex. No. | Compound | MP ° C. |
|---|---|---|
| 1J | S-ethyl-N-(4-methoxyphenyl)isothiourea | 127–128[f] |
| 1K | S-ethyl-N-(2-pyridyl)isothiourea | 161–163[g] |

[a] = Recrystallized from acetone-pentane
[b] = Triturate with pentane
[c] = Triturated with pentane, followed by hot ethyl acetate
[d] = Triturated with hot ethyl acetate
[e] = Recrystallized from acetone-pentane, and then from ethanol-ethyl acetate
[f] = Recrystallized from ethyl acetate-hexane
[g] = Recrystallized from methanol-ether

EXAMPLE 2

Preparation of S-Ethyl-N-[4-trifluoromethyl)phenyl] isothiourea

To a stirred suspension of 1-[4-trifluoromethyl)phenyl]-2-thiourea (3.00 g, 13.6 mmol) in acetone (50 mL) was added iodoethane (6.63 g, 42.5 mmol). The mixture was heated to reflux and stirred overnight. After cooling to room temperature, the mixture was concentrated at reduced pressure. The resulting red viscous oil was poured into saturated $NaHCO_3$ and extracted with ether. The organic layer was dried over magnesium sulphate and filtered. The filtrate was acidified with 1N hydrochloric acid in ether, diluted with pentane and stirred for 20 minutes. The yellow solid was collected and recrystallized from ethanol-ether to afford S-ethyl-N-[4-(trifluoromethyl)phenyl]isothiourea hydrochloride (2.71 g, 70%) as a white solid. Mp=127° C. Anal. Calcd for $C_{10}H_{11}N_2SF_3 \cdot HCl$: C, 42.18; H, 4.25; N, 9.84; S, 11.26; Cl, 12.45. Found: C, 42.22; H, 4.20; N, 9.85; S, 11.20; Cl, 12.43.

The following compounds were made by an analagous method:

| Ex. No | Compound | MP ° C. |
|---|---|---|
| 2A | S-Benzyl-N-[4-(trifluoromethyl)phenyl]isothiourea | 71–72[a] |
| 2B | S-Ethyl-N-(3-chlorophenyl)isothiourea | 95–96[b] |
| 2C | S-Ethyl-N-(2-isopropylphenyl)isothiourea | 66–68[a] |
| 2D | S-Ethyl-N-(4-isopropylphenyl)isothiourea | 113–116[a] |
| 2E | S-Ethyl-N-[3-(trifluoromethyl)phenyl]isothiourea | 102[a] |
| 2F | S-Ethyl-N-[2-(trifluoromethyl)phenyl]isothiourea | 75–77[a] |
| 2G | S-Ethyl-N-[2-(chlorophenyl)isothiourea | 87–90[a] |
| 2H | S-Ethyl-N-(2-methoxyphenyl)isothiourea | 75–78[b] |
| 2I | S-Ethyl-N-(4-methylphenyl)isothiourea | 138–141[a] |
| 2J | S-Ethyl-N-(3-pyridyl)isothiourea | 180–182[c] |
| 2K | S-Ethyl-N-(4-chloro-3-(trifluoromethyl)phenyl) isothiourea | 143[a] |
| 2L | S-Ethyl-N-(2-chloro-5-(trifluoromethyl)phenyl) isothiourea | 155–156[d] |
| 2M | S-Ethyl-N-(4-pyridyl)isothiourea | 151–152[e] |

[a] = Triturated with pentane
[b] = Recrystallised from acetone-pentane
[c] = Recrystallised from ethanol-ether
[d] = Recrystallisation not required
[e] = Free base purified by silica gel chromatography

EXAMPLE 3

Preparation of O-Methyl-N-(4-(trifluoromethyl) phenyl)isourea

To a stirred, cooled (0° C.) solution of 4-aminobenzotrifluoride (1.61 g, 10.0 mmol) in methanol (10 ml) was added a solution of cyanogen bromide (1,17 g, 11.0 mmol) in methanol (10 ml) dropwise. The mixture was allowed to warm to room temperature and stirred for 5 days. The solvent was removed at reduced pressure and the residue was partitioned between diethyl ether and water. The organic layer was dried over sodium sulphate and filtered. Solvent was removed at reduced pressure. The residue was chromatographed on silica gel eluting with 20% ethyl acetate in hexane to give 660 mg of a solid (mp=117–126° C.).

To a stirred, cooled (0° C.) solution of the above solid (172 mg, 0.93 mmol) in methanol (10 ml) was added 1N hydrochloric acid in diethyl ether (0.93 ml, 0.93 mmol). After 20 minutes the mixture was warmed to room temperature, stirred for 10 hours, and concentrated at reduced pressure. The residue was triturated with diethyl ether and filtered to afford 149 mg (63%) of O-Methyl-N-(4-(triluoromethyl)phenyl)isourea as a light beige solid. Mp=121–123° C.

The following compound was prepared by an analagous method:

| | | |
|---|---|---|
| 3A | O-Ethyl-N-(4-(trifluoromethyl)phenyl)isourea | 117–119° C. |

EXAMPLE 4

Preparation of S-Ethyl-N-[4-(trifluoromethoxy) phenyl]isothiourea

To a stirred solution of 4-(trifluoromethoxy)aniline (5.24 g, 2.6 mmol) in acetone (100 ml) was added benzoyl isothiocyanate (5.46 g, 33.5 mmol). After stirring overnight at room temperature, the mixture was concentrated at reduced pressure giving a yellow solid. Recrystallization from ethyl acetate-hexane afforded 9.29 g (92%) of a pale yellow solid. Mp=124–125° C.

To a stirred solution of the above solid (7.80 g, 22.9 mmol) in tetrahydrofuran (100 ml) was added 2.0N aqueous sodium hydroxide (25 ml, 50.0 mmol). The mixture was heated to reflux for 3 h, cooled to room temperature and then concentrated at reduced pressure. The residue was suspended in water and extracted repeatedly with dichloromethane. The combined organic layers were washed with brine and dried over magnesium sulphate. Solvent was removed at reduced pressure giving a solid. Recrystallization from ethyl acetate-hexane afforded 3.77 g (70%) of a white solid. Mp=136–137° C.

To a stirred solution of the above white solid (3.00 g, 12.7 mmol) in acetone (100 ml) was added iodoethane (5.85 g, 37.5 mmol). The mixture was heated to reflux and stirred overnight. After cooling to ambient temperature, the mixture was concentrated at reduced pressure giving an oil. The oil was dissolved in water and washed with pentane. The aqueous layer was poured into saturated aqueous sodium hydrogen carbonate (75 ml) and extracted with ether. The organic layer was dried over magnesium sulphate, concentrated at reduced pressure to a volume of 200 mL and treated with 1N hydrochloric acid (15 ml, 15.0 mmol) in ether. This mixture was stirred for 20 minutes, concentrated at reduced pressure and placed in vacuo overnight to give a gummy foam. Trituration of the foam with pentane gave a solid which was collected and dried in vacuo to afford S-ethyl-N-[4-(trifluoromethoxy) phenyl]isothiourea hydrochloride (3.35 g, 88%) as a white solid. Mp=96–97° C.

EXAMPLE 5

Preparation of $N^5$-(2-thiazoin-2-yl)-L-ornithine

To a solution of N5-carbonylbenzyloxy-N2-tert-butyloxycarbonyl-L-ornithine tert-butyl ester (2.2 g, 5.2 mmol) (Feldman, Tet. Lett. 1991, 32 (7), 875–878) in ethyl acetate (50 ml) was added 10% palladium on carbon (1.0 g). The suspension was shaken at 22° C. under 50 psi $H_2$ for 30 minutes in a 500 ml Parr bottle. The catalyst was removed by filtration through celite. The resulting solution was concentrated to yield the amine intermediate (1.5 g) as a crude oil. To a solution of the amine intermediate in tetrahydrofuran (20 ml) and triethylamine (1 ml) was added chloroethylisothiocyanate (650 mg, 5.35 mmol) as a solution in tetrahydrofaran (10 ml) at 20° C. The mixture was stirred for 16 hours, filtered, concentrated, and purified by silica gel chromatography eluting with ethyl acetate to yield the thiazoline intermediate (1.2 g, 62%) as a white foamy solid. The thiazoline foam was taken up into a mixture of trifluoroacetic acid (9.5 ml), water (0.5 ml), thioanisole (0.5 ml), phenol (0.75 g) and 1,2-ethanediol (0.25 ml) at 0° C. The solution was stirred for two hours at 20° C. and concentrated to a volume of 3 ml. The solution was rapidly stirred and diethyl ether (50 ml) was added. After decanting and washing with ether, the residue was purified by silica gel chromatography (ammonium hydroxide: methanol, gradient, 0:100 to 3:97) to yield $N^5$-(2-thiazolin-2-yl)-L-ornithine (480 mg, 69%) as a white solid, $^1$H NMR (300 MHz, $D_2O$) δ 3.36 (t, J=7.4 Hz, 2H), 3.54 (m,1H), 3.38 (t,J=7.4 Hz, 2H), 3.27 (t, J=6.7Hz, 2H), 1.8–1.55 (m,4H).

The following compound was made by an analagous method:

| 5A | $N^6$-(2-thiazolin-2-yl)-L-lysine |
|---|---|

1H NMR (200 MHz, $D_2O$) δ 3.85(t, J=7.3 Hz, 2H) 3.53 (m, 1H), 3,37 (t, J=7.4 Hz, 2H), 3.24 (t,J=6.8Hz, 2H), 1.8–1.65(m,2H), 1.65–1.5 (m, 2H), 1.45–1.3 (m,2H)

EXAMPLE 6

Preparation of N,N'-((methylthio)iminomethyl)-m-xylylenediamine

To a stirred solution of p-xylene diamine (3.3 ml, 25 mmol) in dichloromethane (100 ml) at 0° C. was added benzoylisothiocyanate (7.0 ml, 52.0 mmol). The reaction mixture was stirred for 16 hours with gradual warming to room temperature. The solvent was removed under reduced pressure and the yellow-coloured solid slurried in hot ethanol to yield a pale yellow solid. This solid was suspended in 100 mL of 10% sodium hydroxide solution and heated to reflux for exactly five minutes. The solution was acidified with concentrated hydrochloric acid, then made basic with concentrated ammonium hydroxide. As the solution cools, an off-white, granular solid forms that is washed with hot 95% ethanol and dried to give a bis-thiourea intermediate (4.82 g). The bis-thiourea intermediate (2.54 g, 10 mmol) was stirred at 22° C. in dimethyl formamide (25 ml) with iodomethane (5.0 ml, 80.0 mmol) for 72 hours. The solution was concentrated to a thick oil and purified by preparative C18 reverse phase chromatography. Elution with 95:5:0.1 water: methanol: trifluoroacetic acid gave an oil. The oil was taken up into hot absolute ethanol and ethyl acetate. Upon cooling, N,N'-((methylthio)iminomethyl)-m-xylyenediamine (4.28 g) was isolated as a white solid (m.p.=164–167° C.).

EXAMPLE 7

Preparation of N,N-((methylthio)iminomethyl)-p-xylylenediamine

The intermediate bis-thiourea (5.92 g) was prepared from p-xylylenediamine (3.4 G, 25 mmol) as described in Example 5. To a solution of the bis-thiourea intermediate (1.27 g, 5 mmol) in dimethylformamide (25 ml) was added iodomethane (2.5 ml, 40 mmol). The solution was stirred at 22° C. for 72 hours, and the solvent was removed under reduced pressure to yield a crude, amber-coloured oil. The crude product was taken up into hot ethanol (40 mL) and treated with 160 mL of ethyl acetate with scratching to induce crystallization. The solution was cooled overnight, filtered, and dried in vacuo at 60° C. for 48 hours to yield N,N-((methylthio)iminomethyl)-p-xylylenediamine (2.29 g, 87%) as a light yellow solid (m.p.=209–212° C.).

EXAMPLE 8

Preparation of $N^5$-(iminomethylthio)methyl-L-ornithine $N^2$-Tertbutoxycarbonyl-L-thiocitrulline tert-butyl ester (Tett. Lett. (1991) 32(7), 875–878) (4 g, 12.0 mmol) was treated with 7.5 mL (120 mmol) iodomethane in 30 mL anhydrous acetonitrile at 20° C. with stirring for 4 hours. The solution was concentrated to a yellow foam and stirred with a 0° C. mixture of trifluoroacetic acid (30 mL), phenol (2.25 g), water (1.0 mL), thioanisole (1.0 mL), and 1,2-ethanedithiol (0.5 mL) for 1.5 hours. The mixture was concentrated under reduced pressure to a volume of 5 mL and 80 mL ether was added with rapid stirring. The resulting grainy residue was washed with ether several times and then dissolved into a minimum amount of methanol (10 mL). A 50/50 solution of ammonium hydroxide and methanol was added until initial spotting on litmus paper indicated a pH of 8. Upon standing at 20° C. for 16 hours, a white precipitate was collected by filtration and dried under reduced pressure at 100° C. to yield $N^5$-(imino(methylthio)methyl-L-ornithine (2.15 g, 56%) as a white solid as the mono-trifluoroacetic acid salt (m.p.=207–208, dec.).

EXAMPLE 9

Preparation of $N^5$-(ethylthio)iminomethyl)-L-ornithine $N^2$-tert-butoxycarbonyl-L-thiocitrulline tert-butyl ester (1.3 g, 3.89 mmol) in 20 mL anhydrous acetonitrile was stirred with 1.21 g (7.75 mmol) iodoethane at 20° C. for 60 hours. The solution was concentrated to a tan-coloured foam (1.75 g). This crude solid was treated at 0° C. with stirring for 2 hours with a solution of 14 mL trifluoroacetic acid, 2.25 g phenol, 1.5 mL thioanisole, 1.5 mL water, and 0.75 mL 1,2-ethanedithiol. The mixture was partially concentrated and 100 mL diethylether was added. The resulting residue was washed with ether several times and purified by silica gel chromatography eluting with methanol followed by 1% ammonium hydroxide in methanol solution. The pooled product fractions were concentrated and passed through a reverse phase C18 column eluting with methanol/water mixtures containing 0.1% heptafluorobutyric acid. After freeze-drying, the material was passed through a second C18 column eluting with methanol/water mixtures containing 0.1% trifluoroacetic acid. Concentration of the pooled product fraction gave 336 mg of the bis-TFA salt (19% overall yield) as a hygroscopic glass. $^1$H NMR (300 MHz, $D_2O$) δ 3.92 (t, J=6.1Hz,1H), 3.41 (t, J=6.6Hz, 2H), 3.09 (q, J=7.3Hz, 2H), 1.95 (m, 2H), 1.75 (m, 2H), 1.32 (t, J=7.3Hz, 3H).

The following compounds were prepared by an analogous method:

9A  $N^6$-(imino(methylthio)methyl)-L-lysine prepared from $N^2$-tert-butoxycarbonyl-L-homothiocitrulline tert-butyl ester
    Mass spectrum (CI) 220 (MH+, 100%)
9B  $N^6$-((ethylthio)iminomethyl)-L-lysine
    Mass spectrum (CI) 234 (MH+, 70%)
9C  $N^5$-(imino(1-methylethylthio)methyl)-L-ornithine
    Mass spectrum (FAB) 234.2 (MH+)
9D  $N^6$-(imino(1-methylethylthio)methyl)-L-lysine
    Mass spectrum (FAB) 248.2 (MH+)
9E  $N^5$-(imino(2-methylpropylthio)methyl)-L-ornithine
    Mass spectrum (FAB) 248.2 (MH+)
9F  $N^6$-(imino(2-methylpropylthio)methyl)-L-lysine
    Mass spectrum (FAB) 262.3 (MH+)
9G  $N^5$-((methylthio)iminomethyl)-D-ornithine
    Mass spectrum (CI) 205.9 (MH+, 79%)
9H  $N^6$-((methylthio)iminomethyl)-D-lysine
    Mass spectrum (CI) 220.0 (MH+, 97%)
9I  $N^5$-((ethylthio)iminomethyl)-D-ornithine
    Mass spectrum (FAB) 220.2 (MH+, 100%)
9J  $N^6$-((ethylthio)iminomethyl)-D-lysine
    Mass spectrum (FAB) 234.0 (MH+, 100%)
9K  $N^5$-(imino(1-methylethylthio)methyl)-D-ornithine
    TLC: 2% $NH_4OH$/MeOH on silica gel, Rf = 0.34
9L  $N^6$-((1-methylethylthio)iminomethyl)-D-lysine
    TLC: 2% $NH_4OH$/MeOH on silica gel, Rf = 0.34
9M  $N^5$((2-methylpropylthio)iminomethyl)-D-ornithine
    Mass spectrum (FAB) 248.1 (MH+, 100%)
9N  $N^6$-((methylpropylthio)iminomethyl)-D-lysine
    TLC: 2% $NH_4OH$/MeOH on silica gel, Rf = 0.38

EXAMPLE 10

Preparation of $N^5$(iminomethoxyethyl)-L-ornithine dihydrochloride a. $N^2$-(tert-butoxycarbonyl)-$N^5$-cyano-L-ornithine tert-butyl ester To a solution of 6.1 g (14.44 mmol) $N^5$-((Benzyloxy)carbonyl)-$N^2$-(tert-butoxycarbonyl)-L-ornithine tert-butyl ester in 100 mL ethyl acetate was added 1.0 g 10% palladium on carbon. The suspension was shaken at 22° C. under 50 psi $H_2$ for 45 minutes in a 500 mL Parr bottle. The catalyst was removed by filtration through celite. The resulting solution was concentrated to yield a crude oil. The oil was dissolved into 50 mL of diethyl ether and added dropwise to a 0° C. stirred solution of 1.52 g (14.3 mmol) of cyanogen bromide in 30 mL ether. The solution was stirred for 2 h, poured into aqueous sodium bicarbonate, and extracted with ether. The ether solution was dried (magnesium sulfate), concentrated, and purified by silica gel chromatography (100 g, 230–400 mesh silica gel). Elution with a gradient of ethyl acetate in hexanes (30%–60%) gave 3.0 g (67% yield) $N^2$-(tert-butoxycarbonyl)-$N^5$-cyano-L-ornithine tert-butyl ester as an oil.

b. $N^2$-(tert-butoxycarbonyl)-$N^5$-(iminomethoxyethyl)-L-ornithine tert-butyl ester hydrochloride To a solution of 1.05 g (3.35 mmol) $N^2$-(tert-butoxycarbonyl)-$N^5$-cyano-L-ornithine tert-butyl ester in 25 mL methanol at 0° C. was added 3.35 mL of 1.0 M hydrochloric acid in ether solution. The solution was stirred overnight (14 h), concentrated, and purified by silica gel chromatography. Elution with a gradient of methanol in dichloromethane (0%–15%) gave 0.95 g (74% yield) $N^2$-(tert-butoxycarbonyl)-$N^5$-(iminomethoxymethyl)-L-ornithine tert-butyl ester hydrochloride.

By the method described above for the preparation of $N^2$-(tert-butoxycarbonyl)-$N^5$-(iminomethoxymethyl)-L-ornithine tert-butyl ester hydrochloride, 1.05 g (3.35 mmol) of $N^2$-(tert-butoxycarbonyl)-$N^5$-cyano-L-ornithine tert-butyl ester produced 0.95 g (75%) $N^2$-(tert-butoxycarbonyl)-$N^5$-(ethoxyiminomethyl)-L-ornithine tert-butyl ester hydrochloride (TLC, silica gel, methanol:dichloromethane/1:4, Rf=0.61) and 1.195 g (3.2 mmol) of $N^2$-(tert-butoxycarbonyl)-$N^5$-cyano-L-ornithine tert-butyl ester produced 0.63 g (63%) $N^2$-(tert-butoxycarbonyl)-$N^5$-(iminoisopropoxymethyl)-L-ornithine tert-butyl ester hydrochloride (TLC, silica gel, methanol: dichloro methane/1:4, Rf=0.53). Mass Spectrum (CI) 360 (MH+, 100%).

c. i) Preparation of $N^5$-(iminomethoxyethyl)-L-ornithine dihydrochloride

A solution of 0.75 g (1.96 mmol) $N^2$-(tert-butoxycarbonyl)-$N^5$-(iminomethoxymethyl)-L-ornithine tert-butyl ester hydrochloride in 2 mL dioxane at 0° C. was treated with 15 mL of 4N hydrochloric acid in dioxane solution. The solution was stirred overnight at 22° C., concentrated to a crude paste, and freeze-dried from 8 mL of water. The product was freeze-dried a second time to yield 0.53 g $N^5$-(iminomethoxymethyl)-L-ornithine dihydrochloride. The product analyzed solvated with an additional 0.2 molar hydrochloric acid. 0.1 molar water, and 0.3 molar dioxane ii) Preparation of $N^5$-(ethoxyiminomethyl)-L-ornithine dihydrochloride.

By the method described above for the preparation of $N^5$-(iminomethoxymethyl)-L-ornithine dihydrochloride, 0.78 g (1.97 mmol) $N^2$-(tert-butoxycarbonyl)-$N^5$-(ethoxyiminomethyl)-L-ornithine tert-butyl ester hydrochloride was deprotected to yield 0.51 g (94%) $N^5$-(ethoxyiminomethyl)-L-ornithine dihydrochloride monohydrate. TLC (silica gel, ammonium hydroxide:methanol/1:25) Rf=0.24. Mass spectrum (CI) 204 (MH+, 74%).

iii) Preparation of $N^5$-(iminomethyl)-L-ornithine dihydrochloride

To a 0° C. stirred solution of 0.54 g (1.32 mmol) $N^2$-(tert-butoxycarbonyl) $N^5$-(iminoisopropoxymethyl)-L-ornithine tert-butyl ester hydrochloride in 2 ml dioxane was added 10 mL of 4N hydrochloric acid in dioxane solution. The solution was stirred 14 h leaving a pale yellow precipitate. The dioxane was removed under reduced pressure and the residue suspended in ether. After stirring for 3 h, the ether was decanted and the solids dried under vacuum to give 0.52 g $N^5$-(iminoisopropoxymethyl)-L-ornithine dihydrochloride. TLC (silica gel, ammonium hydroxide:methanol/1:25) Rf=0.27.

EXAMPLE 11

Preparation of $N^6$-iminomethoxymethyl)-L-lysine dihydrochloride a. $N^2$-(tert-butoxycarbonyl)-$N^6$(cyano)-L-lysine tert-butyl ester $N^6$-((benzyloxy)carbonyl)-$N^2$-(tert-butoxycarbonyl)-L-lysine tert-butyl ester was hydrogenated at 20° C. under 50 psi hydrogen in 100 mL ethyl acetate for 1 h. The catalyst was removed by filtration through celite and the amine intermediate isolated without further purification as an oil (3.05 g). The amine intermediate was taken into 40 mL ether and the solution added over 10 min to a solution of 1.1 g (10.1 mmol) of cyanogen bromide in 50 mL ether at 0° C. The solution was stirred for 2 h, poured into aqueous sodium bicarbonate, dried over magnesium sulfate, and concentrated to give an oil. The crude product was purified by silica gel chromatography eluting with ethyl acetate in hexanes (30%–50%). Concentration gave 2.7 g (80%) of $N^2$-(tert-butoxycarbonyl)-$N^6$-(cyano)-L-lysine tert-butyl ester as a colorless, viscous oil. TLC (silica gel, ethyl acetate:hexanes/1:1)Rf=0.5. IR (neat film) 2222 cm$^{-1}$ (CN). Mass Spectrum (CI 328 (MH$^+$, 44%).

b. $N^2$-(tert-butoxycarbonyl)-$N^2$-(iminomethoxymethyl)-L-lysine tert-butyl ester hydrochloride From 0.86 g (2.63 mmol) $N^2$-(tert-butoxycarbonyl)-$N^6$-(cyano)-L-lysine tert-butyl ester was prepared 0.95 g (91%) $N^2$-(tert-butoxycarbonyl)-$N^6$-(iminomethoxymethyl)-L-lysine tert-butyl ester hydrochloride as a foamy-solid by the method described for the preparation of $N^2$-(tert-butoxycarbonyl)-$N^5$-(iminomethoxymethyl)-L-ornithine tert-butyl ester hydrochloride. TLC (methanol:dichloromethane/1:9) Rf=0.36. Mass spectrum (CI) 360 (MH$^+$, 60%).

From 1.6 g (4.89 mmol) $N^2$-(tert-butoxycarbonyl)-$N^6$-(cyano)-L-lysine tert-butyl ester was prepared 1.5 g (75%) of foamy solid $N^2$-(tert-butoxycarbonyl)-$N^6$-(ethoxyiminomethyl)-L-lysine tert-butyl ester hydrochloride by the method described for $N^2$-(tert-butoxycarbonyl)-$N^5$-(iminomethoxymethyl)-L-ornithine tert-butyl ester hydrochloride. TLC (methanol:dichloromethane/1:9) Rf=0.36. Mass spectrum (CI) 360 (MH$^+$, 60%).

c.(i) $N^6$-(iminomethoxymethyl)-L-lysine dihydrochloride

From 0.70 g (1.77 mmol) $N^2$-(tert-butoxycarbonyl)-$N^6$-(iminomethoxymethyl)-L-lysine tert-butyl ester hydrochloride was prepared 0.38 g (78%) $N^6$-(iminomethoxymethyl)-L-lysine dihydrochloride by the method described above for the preparation of $N^5$-(iminomethoxymethyl)-L-ornithine dihydrochloride TLC (silica gel, ammonium hydroxide:methanol/1:25) Rf=0.24.

c.(ii) $N^6$-(ethoxyiminomethyl)-L-lysine dihydrochloride

From 1.3 g (3.17 mmol) $N^2$-(tert-butoxycarbonyl)-$N^6$-(ethoxyiminomethyl)-L-lysine tert-butyl ester hydrochloride was prepared 0.82 g (89%) $N^6$-(ethoxyiminomethyl)-L-lysine dihydrochloride by the method described above for the preparation of $N^5$-(iminomethoxymethyl)-L-ornithine dihydrochloride. TLC (4% ammonium hydroxide: methanol) Rf=0.24. Mass spectrum (CI) 218 (MH$^+$, 92%).

EXAMPLE 12

Preparation of 1-(3-(Aminomethyl)benzyl)-O-ethylisourea a. Tert-butyl N-(3-(aminomethyl)benzyl)carbamate 10 g (73.42 mmol) of m-xylenediamine was added to 5.1 ml (36.71 mmol) of triethylamine (Kodak) and 200 ml of anhydrous methanol. To this solution at 0° C. was added a solution of 8.0 g (36.71 mmol) of di-t-butyldicarbonate in 60 ml of tetrahydrofuran dropwise over 60 minutes. The solution was stirred and additional two hours at 0° C., filtered, and concentrated to dryness. The crude material was purified by silica gel chromatography eluting with methanol/methylene chloride/ammonium hydroxide (5/95/0.5 to 15/85/0.5) to yield 5.28 g (30%) of a thick, viscous yellow oil.

b. 1-(3-(Aminomethyl)benzyl)-O-ethylisourea 1.2 g (5.08 mmol) of tert-butyl N-(3-(aminomethyl) benzyl)carbamate in 20 ml ether was cooled to 0° C. and 538 mg (5.08 mmol) of cyanogen bromide was added. The mixture was stirred for two hours, poured into saturated sodium bicarbonate solution, and extracted with ether (2×100 ml) and ethyl acetate (100 ml). The organic solutions were dried (sodium sulphate), concentrated, and the resulting crude product was purified by silica gel chromatography. Elution with methylene chloride followed by 5% to 10% methanol in methylene chloride and concentration of the product fractions gave cyanamide intermediate as a white solid (91.08 g, 82% yield). To a solution of 1.0 g (3.83 mmol) of the cyanamide intermediate in 10 ml of ethanol at 0° C, was added 3.83 ml (3.83 mmol) of 1.0M hydrochloric acid solution in anhydrous ether. The solution was stirred for 16 hours, concentrated, and the resulting crude oil was purified by silica gel chromatography eluting with methylene chloride followed by 5% to 20% methanol in methylene chloride to yield 1.22 g (92%) of ethyl acetimidate intermediate as a white coloured foam. To 1.0 g (2.9 mmol) of this foam in 5 ml dioxane chilled to 10° C. was added 10 ml (40 mmol) of 4N hydrochloric acid in dioxane solution. After stirring for 6 hours, most of the solvent was removed under reduced pressure and the residue remaining was treated with 20 ml of ether with rapid stirring. The resulting white solids were collected by filtration to yield 0.73 g (89%) of 1-(3-(Aminomethyl)benzyl)-O-ethylisourea. Mass spectrum (CI) 208.0 (MH$^+$, 68%).

EXAMPLE 13

Preparation of 1-(3-(Aminomethyl)benzyl)-S-methylisothiourea a. Tert-butyl N-(3-((thioureidomethyl)benzyl)carbamate A solution of 0.96 g (4.06 mmol) of tert-butyl N-(3-(aminomethyl)benzyl) carbamate in 20 ml chloroform was added to a 0° C. stirred mixture of 0.975 g (9.75 mmol) calcium carbonate, 0.37 ml (4,87 mmol) thiophosgene, 10 ml water, and 10 ml chloroform. After three hours the mixture was filtered and the aqueous phase was washed with chloroform. The organics were dried (sodium sulphate), concentrated to an oil, and dissolved into 50 ml of anhydrous methanol cooled to 0° C. Ammonia was bubbled for 5 minutes and the solution was stirred for two hours. After concentration to an oil, the crude product was dissolved into 50 ml ethyl acetate, washed with 50 ml water, dried (sodium sulphate), concentrated, and purified by silica gel chromatography eluting with 50% to 80% ethyl acetate in hexanes to provide 0.96 g (80%) of Tert-butyl N-(3-((thioureido) methyl)benzyl)carbamate as a white foam.

b. 1-(3-(Aminomethyl)benzyl)-S-methylisothiourea

A solution of 0.34 g (1.15 mmol) tert-butyl N-(3-((thioureido)methyl)benzyl) carbamate in 25 ml acetonitrile was treated with 0.72 ml (11.51 mmol) iodomethane. The solution was stirred for 22 hours and concentrated to yield 0.49 g (98%) of isothiourea as a foamy solid. This isothiourea intermediate (0.49 g) in 30 ml dioxane was treated with 1.4 ml (5.6 mmol) of 4N hydrochloric acid in dioxane solution. The reaction was stirred for five hours at 20° C. and concentrated. The residue was freeze-dried from water (25 ml) and then purified by preparative reverse phase HPLC eluting with methanol/water/trifluoroacetic acid (5/95/0.1) to yield 260 mg of clear colourless 1-(3 -(Aminomethyl) benzyl)-S-methylisothiourea (46% yield, trifluoroacetic acid salt). Mass Spectrum (CI) 210.0 (MH$^+$, 71.4%)

The following compound was made by an analogous method:

13A 1-(3-(Aminomethyl)benzyl)-S-ethylisothiourea

Mass Spectrum (CI) 224.0 (MH$^+$, 74.6%)

EXAMPLE 14

Preparation of 1-(4-(Aminomethyl)benzyl)-S-metbylisothiourea a. Tert-butyl N-(4-(aminomethyl)benzyl)carbamate To a 0° C. stirred solution of 5.0 g (36.71 mmol) p-xylenediamine in 50 ml tetrahydrofuran and 10 ml tri-ethylamine was added 8.01 g (36.71 mmol) di-t-butyldicarbonate. The solution was stirred for six hours, concentrated, and extracted from water with ethyl acetate. The organics were dried (sodium sulphate) and purified by silica gel chromatography eluting with methanol in methylene chloride (0–60%). Concentration of the product fractions gave 0.96 g (11% yield) of tert-butyl N-(4-(aminomethyl)benzyl)carbamate as a yellow solid.

b. 1-(4-(Aminomethyl)benzyl-S-methylisothiourea

From 2.31 g (9.77 mmol) of tert-butyl N-(4(aminomethyl)benzyl)carbamate was prepared 0.43 g of 1-(4-(Aminomethyl)benzyl)-S-methylisothiourea by the method described in example 13. Mass Spectrum (CI) 209.9 (MH$^+$, 41%).

The following compound was prepared by an analagous method:

14A 1-(4-(Aminomethyl)benzyl)-S-ethylisothiourea

Mass Spectrum (CI) 224.0 (MH$^+$, 60%)

EXAMPLE 15

Biological Activity

The activity of representative compounds of the present invention was determined in accordance with the assay herein described.

Purification of NOS from human placenta

Amion and chorion were removed from fresh placenta, which was then rinsed with 0.9% NaCl. The tissue was homogenized in a Waring blender in 3 volumes of HEDS buffer (20 mM Hepes pH 7.8, 0.1 mM EDTA, 5 mM DTT, 0.2 M sucrose) plus 0.1 mM PMSF. The homogenate was filtered through cheesecloth and then centrifuged at 1000 g for 20 min. The supernatant was recentrifuged at 27500 g for 30 min. Solid ammonium sulfate was added to the supernatant to give 32% saturation. Precipitated protein was pelleted at 25,000 g and then redissolved in a minimal volume of HEDS buffer plus 0.1 mM PMSF, 10 μg/ml leupeptin and soybean trypsin inhibitor, and 1 μg/ml pepstatin. The redissolved pellet was centrifuged at 15000 g for 10 min. To the supernatant was added 1/20 volume of 2',5' ADP agarose resin (Sigma), and the slurry was mixed slowly overnight. In morning, slurry was packed into a column. The resin was sequentially washed with HEDS, 0.5 M NaCl in HEDS, HEDS, and then NOS was eluted with 10 mM NADPH in HEDS. The enzyme could be concentrated by ultrafiltration and quick frozen and stored at –70° C. without loss in activity for at least 6 months.

Assay for human placental NOS

NOS was assayed for the formation of citrulline following the procedure of Schmidt et al (PNAS 88 365–369, 1991) with these modifications: 20 mM Hepes, pH 7.4, 10 μg/ml calmodulin, 2.5 mM CaCl$_2$ 2.5 mM DTT, 125 μM NADPH 10 μM H4 Biopterin, 0.5 mg/ml BSA, and 1 μM L-[14C] arginine (New England Nuclear). Linearity of NOS-catalyzed rate was confirmed prior to kinetic studies that used single time point determination of rate.

Purification of NOS cytokine-induced human colorectal adenocarcinoma DLD-1 cells.

DLD-1 (ATCC No. CCL 221) were groan at 37° C. 5% CO$_2$ in RPMI 1640 medium supplemented with L-glutamin, penicillin, streptomvcin, and 10% heat-inactivated fetal bovine serum. Cells were grown to confluency and then the following cocktail of cytokines were added: 100 units/ml interferon-gamma, 200 units/ml interleukin-6, 10 ng/ml tumor necrosis factor, and 0.5 ng/ml interleukin-1β. At 10–24 hr post-induction, cells were harvested by scraping and washed with phosphate-buffered saline. Pelleted cells were stored at –70° C. Purification of the induced NOS was performed at 4° C. Crude extract was prepared by three cycles of freeze/thawing cells in TDGB (20 mM tris pH 7.5, 10% glycerol, 1 mM DTT, 2 μM tetrahydrobiopterin). Extract was applied directly onto a column of 2',5' ADP sepharse (Pharmacia). Resin was sequentially washed with TDGB, 0.5 M NaCl in TDGB, TDGB. NOS was eluted with 2 mM NADPH in TDGB. BSA was immediately added to give a final concentration of 1 mg/ml. NOS could be quick frozen and stored at –70° C. without loss in activity for at least 2 months.

Assay for inducible human NOS

The formation of citrulline was assayed as described above except that 10 μM FAD was included and calmodulin and CaCl2 were excluded from the assay mix.

Purification of NOS from human brain

Human brain NOS was prepared using variations of the procedures of Schmidt et al. (PNAS 88 365–369, 1991), Mayer et al. (Fed, Eur. Biochem. Soc. 288 187–191, 1991), and Bredt and Snyder, (PNAS 87 682–685, 1990). Briefly, frozen human brain (1050 gm) was homogenized in cold buffer A (50 mM HEPES, pH 7.5 (pH at RT) and 0.5 mM EDTA, 10 mM DTT, 3.6 L total volume) with a polytron. The mixture was centrifuged at 13,000 g for 1 hour and the supernatant was removed (about 2050 ml). To the supernatant, solid ammonium sulfate (365 gm, about 30% of saturation) was added and stirred slowly for a total of 30 minutes. The precipitate was pelleted at 13,000 g for 30 minutes and the pellet was resuspended in ~400 mls of buffer A with 4 μM tetrthydrobiopterin, 1 μM FAD (Sigma), 1 μM FMN (Sigma). The solution was centrifuged at 41,000 g for 60 minutes. The supernatant was removed, frozen by pouring into liquid nitrogen, and stored overnight at –70° C. The mixture was thawed and passed through a 2',5' ADP-agarose column (0.4 g swelled in buffer A) at 4 ml/min. The column was washed with 100 ml buffer A 200 ml buffer A with 500 mM NaCl, 100 ml Buffer A, then 30 ml buffer A with 5 mM NADPH. To the enzyme eluted from the column was added glycerol to 15%. CaCl$_2$ to 1 mM. tetrahydrobiopterin to 10 μM, tween to 0.1% and FAD, FMN to 1 μM each. The enzyme was then passed through a 1 ml calmodulin-agarose column which had been equilibrated in Buffer A, 15% glycerol and 1 mM CaCl$_2$. The column was washed with 15 ml Buffer A, 15% glycerol and 1 mM CaCl$_2$, 15 ml of Buffer A, 15% glycerol and 5 mM EDTA, and then enzyme activity was eluted with 3 ml of Buffer A, 15% glycerol and 5 mM EDTA, 1 M NaCl. To the enzyme was added tetrahydrobiopterin to 10 μM, FAD and FMN to 1 μM, and tween to 0.1%. This solution was concentrated by centriprep-30 to a volume of approximately 500 μl. Human NOS was prepared completely analogously except the calinodulin-agarose column was not used. Enzyme activity was determined as described by Schmidt et al. 1991, except that 10 μM tetrahydrobiopterin was included in the assay. The results are as given in Table 1.

TABLE 1

| Example | Human Inducible Ki/μM | Human Placental Ki/μM | Human Brain Ki/μM |
|---|---|---|---|
| 1 | 3.1 | 4.0 | 0.19 ± 0.01 |
| 1A | 3.2 | 3.1 | 0.56 ± 0.02 |
| 1B | 6.6 | 2.8 | 0.21 ± 0.01 |
| 1C | >25 | 12 | 1.6 |
| 1D | 0 | 14% @25 μm | 30% @25 μm |
| 1E | 44 | 14 | 11 |
| 1F | 4.7 | 2.0 | 0.25 ± 0.02 |
| 1G | 29 | 9.0 | 1.4 ± 0.01 |
| 1H | 28 | 14 | 1.5 ± 0.07 |
| 1I | 2.5 | 2.7 | 0.34 |
| 1J | 4.9 | 2.7 | 0.29 ± 0.04 |
| 1K | 48% @25 μM | 48% @25 μM | 4.8 |
| 2 | 36% @25 μM | 9.4 | 0.32 ± 0.02 |
| 2A | 0 | 0 | 11% @25 μM |
| 2B | 2.4 | 1.8 | 0.45 |
| 2C | 10 | 6.5 | 1.13 ± 0.02 |
| 2D | 25 | 7.7 | 0.33 |
| 2E | 3.2 | 28 | 1.1 ± 0.01 |
| 2F | 22 | 1.8 | 1.4 ± 0.01 |
| 2G | 2.9 | 1.8 | 0.17 |
| 2H | 1.4 | 1.6 | 0.17 ± 0.02 |
| 2I | 1.9 | 1.0 | 0.18 ± 0.04 |
| 2J | 47% @25 μM | 6.9 | 1.0 |
| 2K | 17 | 8.2 | 4.2 |
| 2L | 20% | 6% | 40% |
| 2M | 23 | 6.9 | 1.0 ± 0.2 |
| 2N | 22 | 16 | 0.8 ± 0.2 |
| 3 | 4% | 14% | 24% |
| 3A | 12% | 35% | 1.9 ± 0.1 |
| 5 | 3.3 | 5.5 | |
| 5A | 11 | 21 | |
| 6 | 2.3 | 17 | 0.5 |
| 7 | 45 | 22 | 3.2 |
| 8 | 0.034a | 0.07b | 0.001c |
| 9 | 0.028b | 0.030a | 0.0005c |
| 9A | 1.7 | 4.1 | 0.09 |
| 9B | 0.69 | 3.3 | 3.0 |
| 9C | 0.15 | 2.1 | 0.9 |
| 9D | 22.6 | 23.2 | 28 |
| 9E | 5.3 | 14 | 5.5 |
| 9F | | 79 | 61 |
| 9G | 3.6 | 3.7 | 0.2 |
| 9H | 5.3 | 1.2 | 0.4 |
| 9I | 15 | 11 | 11 |
| 9J | 7.0 | 1.3 | 0.56 |
| 9K | 40 | 30 | 61 |
| 9L | 19 | 23 | 108 |
| 9M | 13 | | 19.5 |
| 9N | | 99 | 61 |
| 10c (i) | 0.22b | 0.12b | 0.10b |
| 10c (ii) | 0.10b | 0.006a | 0.002c |
| 12 | 1.7 | 4.1 | 0.09 |
| 13 | 0.69 | 3.3 | 3.0 |
| 13A | 0.15 | 2.1 | 0.9 |
| 14 | 22.6 | 23.2 | 28 |
| 14A | 5.3 | 14 | 5.5 |

[a]The progress curve was an exponential decay followed by a linear steady state rate. Inhibition constant was calculated by dividing the steady state inhibited rate by the control uninhibited rate; percent inhibition was then used to calculate the inhibition constant assuming competitive inhibition with respect to arginine.
[b]Value obtained from measuring percent inhibition at three or more concentrations of inhibitor at a single time point and assuming competitive inhibition with respect to arginine.
[c]The progress curve was an exponential decay of the rate. Value is a $K_d$ determined by measuring association and dissociation rate constants for the slow onset of inhibition, as previously described (Furfine, E. S., Harmon, M. F., Paith, J. E., and Garvey, E. P. (1993) Biochemistry 32, 8512–8517).

We claim:

1. A method of treatment of a condition requiring selective inhibition of the neuronal NO synthase enzyme comprising administering to a mammal in need thereof a therapeutically effective amount or S-ethyl-N-[(4-trifluoromethyl)phenyl] isothiourea or a salt, ester or amide thereof.

2. A method as claimed in claim 1, wherein the condition is selected from the group consisting of cerebral ischemia, CNS trauma, epilepsy, AIDS dementia, chronic neurodegenerative disease, chronic pain, priapism, obesity, hyperphagia and combinations thereof.

3. A method as claimed in claim 2 wherein the condition is cerebral ischemia.

* * * * *